May 15, 1973 J. M. GARABEDIAN Plant Pat. 3,336
GRAPEVINE
Filed Aug. 26, 1971
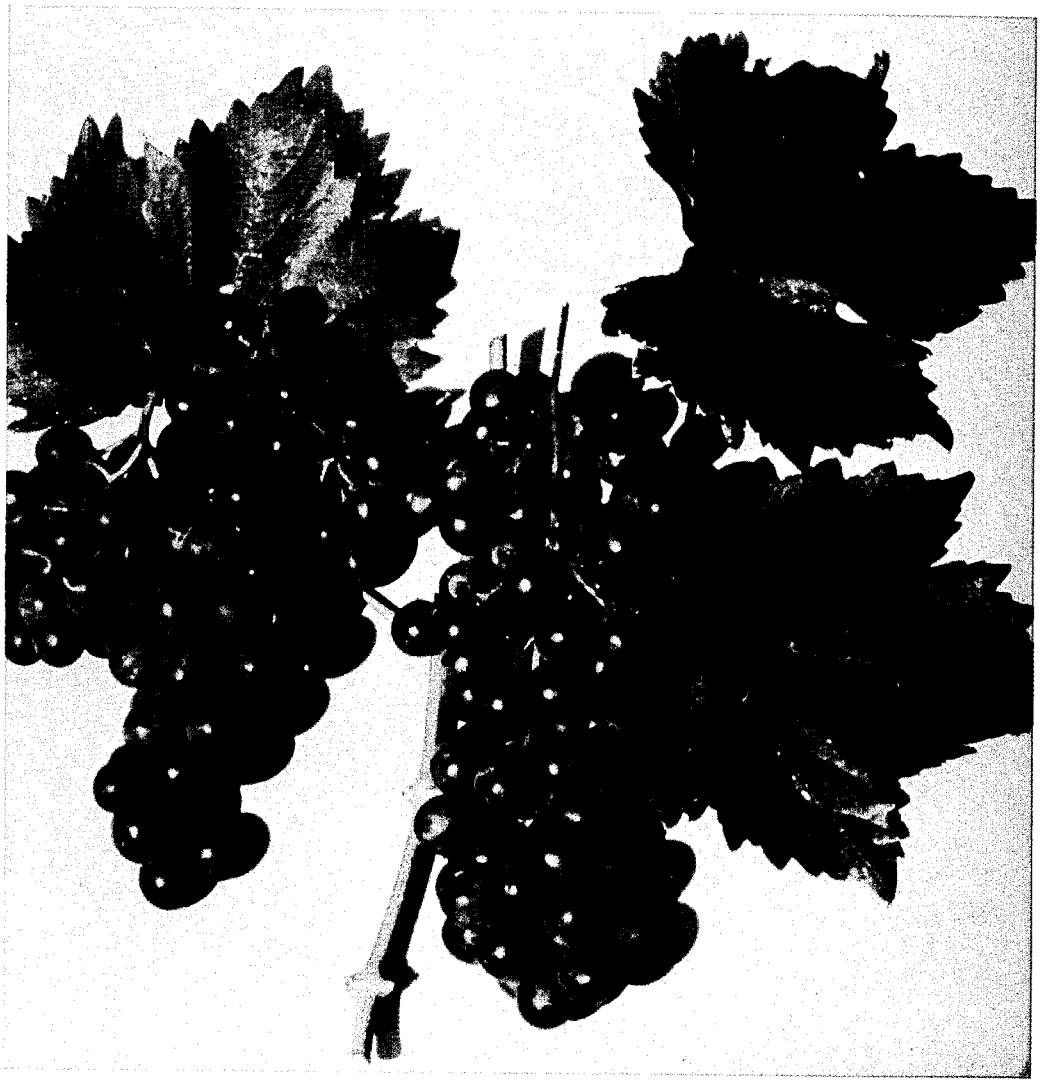

United States Patent Office

Plant Pat. 3,336
Patented May 15, 1973

3,336

GRAPEVINE

John M. Garabedian, 3158 Hamilton St.,
Fresno, Calif. 93712

Filed Aug. 26, 1971, Ser. No. 175,412
Int. Cl. A01h 5/03
U.S. Cl. Plt.—47 1 Claim

ABSTRACT OF THE DISCLOSURE

A grapevine of medium vigor, upright, open, hardy, and productive, with a medium size trunk, straight medium length canes, glabrous cordate leaves of medium size and medium green color, and bearing very early ripening grapes of very good qualtity; the grapes—in harvest maturity approximately three weeks before the Cardinal (unpatented)—being borne in long, tapering clusters of medium size and medium width, and the berries being dark red, strongly adherent, uniform, medium to large size, round to slightly elongated in form, with medium firm, tender, juicy, sprightly, vinous flesh.

ORIGIN OF THE VARIETY

The present variety of grapevine was originated by me, on a ranch of which I am an owner, located near Fresno, Fresno County, Calif., as a cross between the cardinal and Perlette (unpatented). The seedling grapevine, which resulted from the above-described cross, was maintained by me under careful and continuing observation, and—upon the vine bearing fruit—I recognized its new and distinctive characteristics and which classed it as a commercially desirable variety. The variety was, therefore, selected for asexual reproduction preparatory to ultimate commercial planting thereof.

ASEXUAL REPRODUCTION OF THE VARIETY

Subsequent to origination of the present variety of grapevine, and recognition by me of its advantageous characteristics, I asexually reproduced such variety by green-grafting the same on mature Thompson (unpatented) seedless vines in a vineyard on the aforesaid ranch. When grown to maturity, and in bearing, such asexual reproductions ran true to the original grapevine in all respects.

SUMMARY OF THE VARIETY

The herein claimed variety of grapevine is of medium vigor, upright, open, hardy, and productive, with a medium size trunk, straight medium length canes, glabrous cordate leaves of medium size and medium green color, and bearing very early ripening grapes of very good eating quality; the grapes—in harvest maturity approximately three weeks before the Cardinal—being borne in long, tapering clusters of medium size and medium width, and the berries being dark red, strongly adherent, uniform, of medium to large size, and round to slightly elongated in form, with medium firm, tender, juicy, sprightly, vinous flesh.

BRIEF DESCRIPTION OF THE DRAWING

The drawing is an illustration, by photographic reproduction in color, of fruit clusters and leaves of the variety.

DESCRIPTION OF THE VARIETY

The botanical details of this new and distinct variety of grapevine—with color definitions (except those in common color terms) referenced to Maerz and Paul Dictionary of Color—are as follows:

Vine:
- *Vigor.*—Medium.
- *Growth.*—Upright, open, hardy.
- *Production.*—Productive.

Trunk: Medium size, medium caliber.
- *Bark.*—Adherent, shreddy.

Canes: Medium length, medium number, medium thickness to slender, usually straight, brown.
- *Nodes.*—Slightly enlarged, flattened.
- *Internodes.*—Medium length.
- *Tendrils.*—Intermittent, medium thickness to slender, long, bifurcated—some trifurcated; smooth.

Flowers: Fertile.
- *Blooming period.*—Early.
- *Date of first bloom.*—May 15, 1971.
- *Date of last bloom.*—May 23, 1971.
- *Stamens.*—Upright.

Leaves:
- *Size.*—Medium.
- *Form.*—Cordate.
- *Thickness.*—Medium.
- *Color.*—Upper surface—dull medium green (23–L–8); lower surface—pale green (22–K–7).
- *Texture.*—Smooth.
- *Pubescence.*—Mostly glabrous.
- *Lobes.*—Number—5, terminal lobe—acute to acuminate.
- *Petiolar sinus.*—Medium to shallow, wide.
- *Basal sinus.*—Shallow—few medium, narrow.
- *Lateral sinus.*—Shallow, narrow.
- *Margin.*—Dentate.
- *Teeth.*—Medium depth, wide to medium.

Fruit:
- *Ripening period.*—Very early—approximately three weeks before Cardinal.
- *Date of first picking* (Fresno County, Calif.)—July 1, 1971.
- *Date of last picking* (Fresno County, Calif.)—July 11, 1971.
- *Keeping quality.*—Good.
- *Shipping quality.*—Good.
- *Cluster.*—Medium size, medium length, medium breadth, tapering, irregular, single to double shouldered, loose.
- *Peduncle.*—Medium length, medium thickness.
- *Pedicel.*—Medium length, medium thickness—some slender; no warts.
- *Brush.*—Medium length, greenish.
- *Berries.*—Strongly adherent, medium to large, uniform, round to slightly elongated; slightly flat at stem end.
- *Color.*—Dark red (8–L–4), with medium grey (47–A–2) bloom.
- *Skin.*—Medium thick, tough, adheres to pulp.
- *Flesh.*—Greenish with red directly under skin, translucent, medium texture, tender, juicy, juice—clear, sprightly, vinous; quality—very good.
- *Sacchrometer test.*—Average—17% solids.
- *Seeds.*—Separates from pulp easily, number—1–4—average 2.5; medium to small, medium length, medium breadth; slightly beaked, green (20–K–2).
- *Raphe.*—Medium to cord-like.
- *Chalaza.*—Below center, oval, distinct, sunken.
- *Use.*—Dessert, kitchen market.

The grapevine and its fruit herein described may vary in slight detail due to climatic and soil conditions under which the variety may be grown; the present description being of the variety as grown in the Central Valley of California.

I claim:

1. A new and distinct variety of grapevine, substantially as illustrated and described, which is of medium vigor, upright, open, hardy, and productive, with a medium size trunk, straight medium length canes, glabrous cordate leaves of medium size and medium green color, and bearing very early ripening grapes of very good eating quality; the grapes—in harvest maturity approximately three weeks before the Cardinal—being borne in long, tapering clusters of medium size and medium width, and the berries being dark red, strongly adherent, uniform, of medium to large size, and round to slightly elongated in form, with medium firm, tender, juicy, sprightly, vinous flesh.

No references cited.

ROBERT E. BAGWILL, Primary Examiner